United States Patent [19]
Beier et al.

[11] Patent Number: 5,972,702
[45] Date of Patent: *Oct. 26, 1999

[54] OSTEOCLAST TRANSPORTER

[75] Inventors: David R. Beier, Brookline; Kevin P. Brady, Boston, both of Mass.

[73] Assignee: The Brigham and Women's Hospital, Inc., Boston, Mass.

[*] Notice: This patent issued on a continued prosecution application filed under 37 CFR 1.53(d), and is subject to the twenty year patent term provisions of 35 U.S.C. 154(a)(2).

[21] Appl. No.: 08/647,397

[22] Filed: May 9, 1996

[51] Int. Cl.$^6$ .............................. C12N 5/00; C07H 21/04
[52] U.S. Cl. ...................... 435/325; 536/23.5; 536/24.1
[58] Field of Search .......................... 435/325; 536/23.1, 536/24.31, 23.5, 24.1

[56] References Cited

PUBLICATIONS

Reddi, A. H. Cellular and molecular approaches to osteoporosis. Curr. Opin. in Orthopedics. vol. 6:50–54, Jan. 1995.

Orkin et al. Report and recommendation of the panel to assess the NIH investment in research on gene therapy, Dec. 7, 1995.

Evans et al. Possible orthopaedic application of gene therapy. J. Bone and Joint Surg. vol. 77–A(7):1103–1114, Jul. 1995.

Turner et al. Primary sequence of paxillin contains putative SH2 and SH3 domain binding motifs and multiple LIM domains: identification of a vinculin and pp125fak binding region. J. Cell Sci. vol. 107:1582–1591, Jul. 1994.

Azuhata et al. Close similarity between genome structures of rice black–streaked dwarf and maize rough dwarf viruses. J. Gen. Virol. vol. 74:1227–1232, Jul. 1993.

Grundemann, et al., Nature 372:549–552, 1994.

Takahashi, et al., Endocrinology 122:1373–1382, 1988.

Boyce, et al., J. Clin. Invest. 90:1622–1627, 1992.

EMBL database entry Hs345165. Accession No. H20345 (1995).

EMBL database entry Hs581185. Accession No. H41581 (1995).

EMBL database entry Mm52842. Accession No. U52842 (1996).

Marger et al *TIBS* 18:13–20, 1993.

Grundemann, et al., Nature 372:549–552, 1994.

Beier et al., *The American Journal of Human Genetics* 59:A280 (1996).

EMBL database entry MMAA8584. Accession No. AA108584 (1996).

*Primary Examiner*—Nancy Degen
*Assistant Examiner*—William Sandals
*Attorney, Agent, or Firm*—Wolf, Greenfield & Sacks, P.C.

[57] ABSTRACT

The invention pertains to osteoclast transporter proteins and genes encoding such proteins, as well as fragments and biologically functional variants thereof. The invention also pertains to therapeutics and diagnostics involving the foregoing proteins and genes and agents that bind the foregoing proteins and genes, to influence osteoclast activity and bone remodeling.

12 Claims, 1 Drawing Sheet

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 2102 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (v) FRAGMENT TYPE: internal (vi) ORIGINAL SOURCE:
      (A) ORGANISM: Mus musculus (ix) FEATURE:
      (A) NAME/KEY: CDS
      (B) LOCATION: 120..1733

(xi) SEQUENCE DESCRIPTION: SEQ ID NO:1:

```
TGCGAGCGTG CTACTACAGC AGCTGCTGAA CCTAGACAGG CACGGCAACT GCTGCATCCA      60

GCTCCAGCCC AACTGAATCC AGCTCCAACC ACCAGTTTTG GTTCATCTTG CCTGGTGCC      119
```

```
ATG ACC TTC TCC GAG ATT CTG GAC CGT GTT GGA AGC ATG GGC CCC TTC       167
Met Thr Phe Ser Glu Ile Leu Asp Arg Val Gly Ser Met Gly Pro Phe
 1               5                  10                  15

CAG TAC CTG CAT GTG ACC TTG CTG GCC CTC CCA ATC CTC GGA ATA GCC       215
Gln Tyr Leu His Val Thr Leu Leu Ala Leu Pro Ile Leu Gly Ile Ala
             20                  25                  30

AAC CAC AAC TTG CTA CAG ATC TTC ACA GCC ACC ACC CCT GAC CAC CAC       263
Asn His Asn Leu Leu Gln Ile Phe Thr Ala Thr Thr Pro Asp His His
         35                  40                  45

TGT CGC CCG CCC CCC AAC GCC TCT CTA GAG CCC TGG GTA CTC CCC TTG       311
Cys Arg Pro Pro Pro Asn Ala Ser Leu Glu Pro Trp Val Leu Pro Leu
 50                  55                  60

GGC CCA AAC GGG AAG CCT GAG AAG TGT CTC CGC TTC GTG CAT CTG CCA       359
Gly Pro Asn Gly Lys Pro Glu Lys Cys Leu Arg Phe Val His Leu Pro
 65                  70                  75                  80

AAC GCC AGT CTT CCC AAT GAC ACC CAG GGG GCC ACC GAG CCA TGC TTG       407
Asn Ala Ser Leu Pro Asn Asp Thr Gln Gly Ala Thr Glu Pro Cys Leu
                 85                  90                  95

GAT GGC TGG ATC TAC AAC AGC ACC AGA GAC ACC ATT GTG ACA GAG TGG       455
Asp Gly Trp Ile Tyr Asn Ser Thr Arg Asp Thr Ile Val Thr Glu Trp
             100                 105                 110

GAC TTG GTA TGC GGC TCC AAC AAA CTG AAG GAG ATG GCA CAG TCA GTC       503
Asp Leu Val Cys Gly Ser Asn Lys Leu Lys Glu Met Ala Gln Ser Val
         115                 120                 125

TTC ATG GCA GGT ATA CTG GTT GGA GGA CCT GTG TTT GGA GAA CTG TCA       551
Phe Met Ala Gly Ile Leu Val Gly Gly Pro Val Phe Gly Glu Leu Ser
     130                 135                 140

GAC AGG TTT GGC CGC AAG CCC ATC CTG ACC TGG AGC TAT CTC TTG CTG       599
Asp Arg Phe Gly Arg Lys Pro Ile Leu Thr Trp Ser Tyr Leu Leu Leu
145                 150                 155                 160

GCA GCC AGT GGC TCC AGT GCT GCC TTC AGC CCC AGC CTC ACT GTC TAT       647
Ala Ala Ser Gly Ser Ser Ala Ala Phe Ser Pro Ser Leu Thr Val Tyr
                 165                 170                 175

ATG ATC TTC CGA TTC CTG TGT GGC TGC AGC ATC TCG GGC ATT TCT CTG       695
Met Ile Phe Arg Phe Leu Cys Gly Cys Ser Ile Ser Gly Ile Ser Leu
             180                 185                 190

AGC ACC ATT ATC TTG AAT GTG GAA TGG GTA CCC ACC TCC ACG CGG GCC       743
Ser Thr Ile Ile Leu Asn Val Glu Trp Val Pro Thr Ser Thr Arg Ala
         195                 200                 205

ATC TCA TCA ACA ACT ATT GGG TAC TGC TAC ACC ATT GGT CAA TTC ATT       791
Ile Ser Ser Thr Thr Ile Gly Tyr Cys Tyr Thr Ile Gly Gln Phe Ile
     210                 215                 220

CTG CCT GGC CTG GCC TAT GCC GTT CCT CAG TGG CGC TGG CTA CAG TTG       839
Leu Pro Gly Leu Ala Tyr Ala Val Pro Gln Trp Arg Trp Leu Gln Leu
225                 230                 235                 240

TCC GTG TCT GCT GCC TTC TTC ATC TTC TCC TTG TTG TCC TGG TGG GTA       887
Ser Val Ser Ala Ala Phe Phe Ile Phe Ser Leu Leu Ser Trp Trp Val
                 245                 250                 255

CCA GAG TCC ATA CGC TGG CTG GTT CTG TCT GGA AAA TTC TCA CGA GCT       935
Pro Glu Ser Ile Arg Trp Leu Val Leu Ser Gly Lys Phe Ser Arg Ala
             260                 265                 270

CTG AAG ACA CTC CAA CGT GTG GCT ACC TTC AAC GGC AAG AAG GAG GAA       983
Leu Lys Thr Leu Gln Arg Val Ala Thr Phe Asn Gly Lys Lys Glu Glu
         275                 280                 285

GGG GAA AAG CTC ACT GTG GAG GAG CTG AAG TTC AAC TTG CAG AAG GAC      1031
Gly Glu Lys Leu Thr Val Glu Glu Leu Lys Phe Asn Leu Gln Lys Asp
     290                 295                 300

ATC ACC TCA GCC AAG GTC AAA TAT GGC TTA TCT GAC TTG TTC CGA GTG      1079
Ile Thr Ser Ala Lys Val Lys Tyr Gly Leu Ser Asp Leu Phe Arg Val
305                 310                 315                 320
```

```
TCC ATC CTG CGC CGT GTG ACC TTC TGT CTC TCT CTG GCC TGG TTT GCT      1127
Ser Ile Leu Arg Arg Val Thr Phe Cys Leu Ser Leu Ala Trp Phe Ala
            325                     330                     335

ACT GGC TTT GCC TAC TAC AGT TTG GCT ATG GGA GTA GAA GAA TTT GGA      1175
Thr Gly Phe Ala Tyr Tyr Ser Leu Ala Met Gly Val Glu Glu Phe Gly
            340                     345                     350

GTC AAC ATC TAC ATA CTC CAG ATC ATC TTC GGT GGG GTT GAC ATT CCC      1223
Val Asn Ile Tyr Ile Leu Gln Ile Ile Phe Gly Gly Val Asp Ile Pro
            355                     360                     365

GCC AAG TTC ATC ACA ATC CTC TCC ATA AGT TAT CTG GGC CGG CGC ATC      1271
Ala Lys Phe Ile Thr Ile Leu Ser Ile Ser Tyr Leu Gly Arg Arg Ile
            370                     375                     380

ACT CAG GGC TTC CTC CTG ATC CTG GCA GGA GTG GCC ATC CTG GCC CTC      1319
Thr Gln Gly Phe Leu Leu Ile Leu Ala Gly Val Ala Ile Leu Ala Leu
385                     390                     395                 400

ATC TTT GTG TCT TCA GAA ATG CAG CTC TTG AGA ACA GCA CTG GCT GTA      1367
Ile Phe Val Ser Ser Glu Met Gln Leu Leu Arg Thr Ala Leu Ala Val
            405                     410                     415

TTT GGG AAG GGA TGC CTG TCT GGC TCC TTC AGC TGC CTC TTC CTC TAC      1415
Phe Gly Lys Gly Cys Leu Ser Gly Ser Phe Ser Cys Leu Phe Leu Tyr
            420                     425                     430

ACA AGT GAG CTC TAC CCT ACA GTC CTC AGG CAA ACA GGT ATG GGT ATC      1463
Thr Ser Glu Leu Tyr Pro Thr Val Leu Arg Gln Thr Gly Met Gly Ile
            435                     440                     445

AGT AAC ATA TGG GCT CGA GTG GGA AGT ATG ATA GCC CCA CTG GTG AAA      1511
Ser Asn Ile Trp Ala Arg Val Gly Ser Met Ile Ala Pro Leu Val Lys
            450                     455                     460

ATC ACG GGA GAA CTG CAG CCC TTC ATC CCT AAT GTC ATC TTT TGG ACC      1559
Ile Thr Gly Glu Leu Gln Pro Phe Ile Pro Asn Val Ile Phe Trp Thr
465                     470                     475                 480

ATG ACT CTA CTG GGA GGC AGT GCT GCC TTC TTT CTG CTT GAG ACC CTC      1607
Met Thr Leu Leu Gly Gly Ser Ala Ala Phe Phe Leu Leu Glu Thr Leu
            485                     490                     495

AAT CGG CCC TTA CCA GAA ACT ATC GAG GAC ATA CAA GAC TGG TAC CAG      1655
Asn Arg Pro Leu Pro Glu Thr Ile Glu Asp Ile Gln Asp Trp Tyr Gln
            500                     505                     510

CAA ACC AAG AAA ACA AAG CAG GAG CCA GAA GCA GAA AAG GCA TCC CAG      1703
Gln Thr Lys Lys Thr Lys Gln Glu Pro Glu Ala Glu Lys Ala Ser Gln
            515                     520                     525

ACA ATC CCG CTG AAG ACT GGT GGA CCC TAGCTAAGAA CAACAGAATC            1750
Thr Ile Pro Leu Lys Thr Gly Gly Pro
            530                     535

CTCTTTCCTG CCTTCCAGAG ACTGATCCCA AGCAGGGCCC TTCCAAGGCT ATTCGAGCAC    1810

CTTAGGGGTT GGGTGGAGCC CCAGCTGGCT CCATGCTCTC AGAACAAAGA CTTCTGAGAG    1870

TTCAGCAAAA GTGTTTTACC TTCACCACCT CCACCGTAGC CCACAACCCA GACCTGGCCT    1930

GTTCACAGCC CTAGCCATAC TCACTCCTGC ACTCATCCTC CCTGCAACCC AGGCCCTGCC    1990

ATTTTTCTCT ACCCTCTTTG TATTGGCCAT TTCCTCCATT GTCCCACCTC CATTTCCCTT    2050

TGAGATTCCC TGGCAGTTCT AATGGTTTCC TCTTACCCTC CCCCTCGTGC CG            2102

(2) INFORMATION FOR SEQ ID NO:2:

(i) SEQUENCE CHARACTERISTICS:
        (A) LENGTH: 537 amino acids
        (B) TYPE: amino acid
        (D) TOPOLOGY: linear (ii) MOLECULE TYPE: protein (xi) SEQUENCE DESCRIPTION: SEQ ID NO:2:
```

-continued

```
Met Thr Phe Ser Glu Ile Leu Asp Arg Val Gly Ser Met Gly Pro Phe
 1               5                  10                  15

Gln Tyr Leu His Val Thr Leu Ala Leu Pro Ile Leu Gly Ile Ala
             20                  25                  30

Asn His Asn Leu Leu Gln Ile Phe Thr Ala Thr Thr Pro Asp His His
             35                  40                  45

Cys Arg Pro Pro Pro Asn Ala Ser Leu Glu Pro Trp Val Leu Pro Leu
 50                  55                  60

Gly Pro Asn Gly Lys Pro Glu Lys Cys Leu Arg Phe Val His Leu Pro
 65                  70                  75                  80

Asn Ala Ser Leu Pro Asn Asp Thr Gln Gly Ala Thr Glu Pro Cys Leu
             85                  90                  95

Asp Gly Trp Ile Tyr Asn Ser Thr Arg Asp Thr Ile Val Thr Glu Trp
             100                 105                 110

Asp Leu Val Cys Gly Ser Asn Lys Leu Lys Glu Met Ala Gln Ser Val
             115                 120                 125

Phe Met Ala Gly Ile Leu Val Gly Gly Pro Val Phe Gly Glu Leu Ser
             130                 135                 140

Asp Arg Phe Gly Arg Lys Pro Ile Leu Thr Trp Ser Tyr Leu Leu Leu
145                 150                 155                 160

Ala Ala Ser Gly Ser Ser Ala Ala Phe Ser Pro Ser Leu Thr Val Tyr
             165                 170                 175

Met Ile Phe Arg Phe Leu Cys Gly Cys Ser Ile Ser Gly Ile Ser Leu
             180                 185                 190

Ser Thr Ile Ile Leu Asn Val Glu Trp Val Pro Thr Ser Thr Arg Ala
             195                 200                 205

Ile Ser Ser Thr Thr Ile Gly Tyr Cys Tyr Thr Ile Gly Gln Phe Ile
             210                 215                 220

Leu Pro Gly Leu Ala Tyr Ala Val Pro Gln Trp Arg Trp Leu Gln Leu
225                 230                 235                 240

Ser Val Ser Ala Ala Phe Phe Ile Phe Ser Leu Leu Ser Trp Trp Val
             245                 250                 255

Pro Glu Ser Ile Arg Trp Leu Val Leu Ser Gly Lys Phe Ser Arg Ala
             260                 265                 270

Leu Lys Thr Leu Gln Arg Val Ala Thr Phe Asn Gly Lys Lys Glu Glu
             275                 280                 285

Gly Glu Lys Leu Thr Val Glu Glu Leu Lys Phe Asn Leu Gln Lys Asp
             290                 295                 300

Ile Thr Ser Ala Lys Val Lys Tyr Gly Leu Ser Asp Leu Phe Arg Val
305                 310                 315                 320

Ser Ile Leu Arg Arg Val Thr Phe Cys Leu Ser Leu Ala Trp Phe Ala
             325                 330                 335

Thr Gly Phe Ala Tyr Tyr Ser Leu Ala Met Gly Val Glu Glu Phe Gly
             340                 345                 350

Val Asn Ile Tyr Ile Leu Gln Ile Ile Phe Gly Gly Val Asp Ile Pro
             355                 360                 365

Ala Lys Phe Ile Thr Ile Leu Ser Ile Ser Tyr Leu Gly Arg Arg Ile
             370                 375                 380

Thr Gln Gly Phe Leu Leu Ile Leu Ala Gly Val Ala Ile Leu Ala Leu
385                 390                 395                 400

Ile Phe Val Ser Ser Glu Met Gln Leu Leu Arg Thr Ala Leu Ala Val
             405                 410                 415

Phe Gly Lys Gly Cys Leu Ser Gly Ser Phe Ser Cys Leu Phe Leu Tyr
```

```
                   420              425               430
      Thr Ser Glu Leu Tyr Pro Thr Val Leu Arg Gln Thr Gly Met Gly Ile
              435             440             445

Ser Asn Ile Trp Ala Arg Val Gly Ser Met Ile Ala Pro Leu Val Lys
              450             455             460

Ile Thr Gly Glu Leu Gln Pro Phe Ile Pro Asn Val Ile Phe Trp Thr
      465             470             475                         480

Met Thr Leu Leu Gly Gly Ser Ala Ala Phe Phe Leu Leu Glu Thr Leu
                      485             490                     495

Asn Arg Pro Leu Pro Glu Thr Ile Glu Asp Ile Gln Asp Trp Tyr Gln
                      500             505             510

Gln Thr Lys Lys Thr Lys Gln Glu Pro Glu Ala Glu Lys Ala Ser Gln
              515             520             525

Thr Ile Pro Leu Lys Thr Gly Gly Pro
              530             535
```

(2) INFORMATION FOR SEQ ID NO:3:

(i) SEQUENCE CHARACTERISTICS:
        (A) LENGTH: 328 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:3:

```
AAGTTCATCA CCATCCTCTC CTTAAGCTAC CTGGGCCGGC ATACCACTCA GGCCGCTGCC    60

TGCTCCTGGC AGGAGGGGCC ATCTTGGCTC TCACCTTTTG CCCTTGGACT TGCAGACCGT   120

GAGACAGTAT TGGCTGTGTT TGGGAAGGGA TGCCTATCCA GCTCCTTCAG CTGCCTCTTC   180

CTCTACACAA GTGAATTATA CCCCACAGTC ATCAGGCAAA CAGGTATGGG CGTAAGTAAC   240

CTGTGGACCC GCGTGGGAAG CATGGTGTCC CGCTGGTGAA ATCACGGGT GAGGTACAGC    300

CCTTCATCCC CAATATCATC TACGGGAT                                     328
```

(2) INFORMATION FOR SEQ ID NO:4:

(i) SEQUENCE CHARACTERISTICS:
        (A) LENGTH: 109 amino acids
        (B) TYPE: amino acid
        (C) STRANDEDNESS: single
        (D) TOPOLOGY: linear (ii) MOLECULE TYPE: protein (iii) HYPOTHETICAL: YES (iv) ANTI-SENSE: NO (v) FRAGMENT TYPE: internal (vi) ORIGINAL SOURCE:
        (A) ORGANISM: Homo sapiens (xi) SEQUENCE DESCRIPTION: SEQ ID NO:4:

```
Lys Phe Ile Thr Ile Leu Ser Leu Ser Tyr Leu Gly Arg His Thr Thr
1               5                   10                  15
```

```
Gln Ala Ala Ala Leu Leu Leu Ala Gly Gly Ala Ile Leu Ala Leu Thr
            20                  25                  30

Phe Xaa Pro Leu Asp Leu Gln Thr Val Arg Thr Val Leu Ala Val Phe
        35                  40                  45

Gly Lys Gly Cys Leu Ser Ser Ser Phe Ser Cys Leu Phe Leu Tyr Thr
 50                  55                  60

Ser Glu Leu Tyr Pro Thr Val Ile Arg Gln Thr Gly Met Gly Val Ser
 65                  70                  75                  80

Asn Leu Trp Thr Arg Val Gly Ser Met Val Ser Xaa Leu Val Lys Ile
                85                  90                  95

Thr Gly Glu Val Gln Pro Phe Ile Pro Asn Ile Ile Tyr
            100                 105
```

(2) INFORMATION FOR SEQ ID NO:5:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:
        (A) ORGANISM: Mus musculus (xi) SEQUENCE DESCRIPTION: SEQ ID NO:5:

```
Asp Arg Phe Gly Arg Lys
 1               5
```

(2) INFORMATION FOR SEQ ID NO:6:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: YES (iv) ANTI-SENSE: NO (v) FRAGMENT TYPE: internal (ix) FEATURE:
        (A) NAME/KEY: Region
        (B) LOCATION: 2
        (D) OTHER INFORMATION: /note= "Xaa at position 2 is Arg or
           Lys"

(ix) FEATURE:
        (A) NAME/KEY: Region
        (B) LOCATION: 5
        (D) OTHER INFORMATION: /note= "Xaa at position 5 is Arg or
           Lys"

(xi) SEQUENCE DESCRIPTION: SEQ ID NO:6:

```
Asp Xaa Xaa Arg Xaa
 1           5
```

OSTEOCLAST TRANSPORTER

This work was funded in part by the NIDDK under Grant Number R01 DK45639. The government may have certain rights to this invention.

This invention relates to osteoclast transporter genes, proteins coded for by such genes, and diagnostics and therapeutics related to medical conditions associated with such genes and proteins, including osteoporosis and osteopetrosis.

BACKGROUND OF THE INVENTION

The remodeling of bone is a dynamic process. Cells continuously lay down and resorb bone material. An imbalance in the activity of cells that lay down new bone (osteoblasts) and cells that resorb bone (osteoclasts) can result in serious, and sometimes even fatal, disorders.

Osteoporosis is a term used for a number of diseases of diverse etiology, all involving a reduction in the mass of bone per unit volume. Osteoporosis is the most common of the metabolic bone diseases. Twenty-five million people in the United States and more than two hundred million people worldwide are affected by osteoporosis. Osteoporosis is frequent among post-menopausal women and is an important cause of morbidity in the elderly. It commonly results in bone fractures, and death can be a frequent occurance in the months following fractures, particularly those of the hip in elderly individuals.

Osteopetrosis is a disorder involving an increase in the mass of bone per unit volume. Its incidence is rare compared to osteoporosis, but it typically is life threatening. Despite having multiple causes, a defect in bone resorption is always the underlying mechanism. In many instances, the disorder is inherited as an autosomal recessive trait and involves abnormal osteoclast function. Bone marrow transplants from normal donors have been attempted to restore normal osteoclast precursor cells, but this therapy has shown only limited success.

Present treatments for osteoporosis and osteopetrosis are inadequate.

There exists a need to influence favorably the bone remodeling process to treat osteoporosis and osteopetrosis. There also exists a need to identify the gene(s) responsible for osteopetrosis and to provide a genetic therapy for treating osteopetrosis.

An object of the invention is to provide compounds that desirably influence the bone remodeling process.

Another object of the invention is to provide therapeutics for treating osteoporosis.

Another object of the invention is to provide therapeutics for treating osteopetrosis.

Still another object of the invention is to provide diagnostics and research tools relating to osteoporosis and osteopetrosis. These and other objects will be described in greater detail below.

SUMMARY OF THE INVENTION

The invention involves in one respect the discovery of osteoclast transporter proteins and nucleic acid molecules encoding those proteins. The expression and biological activity of the proteins are necessary for normal osteoclast function, and alteration of the expression or biological activity of these proteins can be used to influence osteoclast activity and thereby affect bone remodeling. In addition, normal osteoclast function can be established in abnormal osteoclasts lacking a normal osteoclast transporter protein by supplying to the abnormal osteoclast a nucleic acid expressing a functional osteoclast transporter protein.

The preferred nucleic acids of the invention are homologs and alleles of the nucleic acids of SEQ.ID.NO. 1 and SEQ.ID.NO. 3. The invention further embraces functional equivalents, variants, analogs and fragments of the foregoing nucleic acids and also embraces proteins and peptides coded for by any of the foregoing.

According to one aspect of the invention, an isolated nucleic acid molecule is provided. The molecule hybridizes under stringent conditions to a molecule consisting of the nucleic acid sequence of SEQ.ID.NO. 1 and it codes for an osteoclast transporter molecule. The invention further embraces nucleic acid molecules that differ from the foregoing isolated nucleic acid molecules in codon sequence due to the degeneracy of the genetic code. The invention also embraces complements of the foregoing nucleic acids.

According to another aspect of the invention, isolated nucleic acid molecules are provided which hybridize under stringent conditions to a molecule consisting of the nucleic acid sequence of SEQ.ID.NO. 3 and which code for an osteoclast transporter molecule, as well as nucleic acid molecules that differ from such molecules in codon sequence due to the degeneracy of the genetic code. The invention also embraces complements of the foregoing nucleic acids.

Preferred isolated nucleic acid molecules are those comprising the human cDNAs or gene corresponding to SEQ.ID.NO. 3 and the cDNAs or gene corresponding to SEQ.ID.NO. 1.

The invention in another aspect involves expression vectors, and host cells transformed or transfected with such expression vectors, comprising the nucleic acid molecules described above. In one embodiment of the invention, the host cell is a hematopoietic osteoclast precursor cell, such as a stem cell.

According to another aspect of the invention, an isolated nucleic acid molecule is provided which comprises a unique fragment of SEQ.ID.NO. 1 between 12 and 1974 nucleotides in length or a unique fragment of SEQ.ID.NO. 3 between 12 and 360 nucleotides in length, and complements thereof. In one embodiment, the unique fragment is at least 150 and more preferably at least 200 nucleotides in length. In another embodiment, the unique fragment is between 12 and 32 contiguous nucleotides in length.

According to another aspect of the invention, isolated polypeptides coded for by the isolated nucleic acid molecules described above also are provided as well as functional equivalents, variants, analogs and fragments thereof. In one embodiment, the polypeptide is a human osteoclast transporter protein or a functionally active fragment or variants thereof.

The invention also provides isolated polypeptides which selectively bind an osteoclast transporter protein or fragments thereof. Isolated binding polypeptides include antibodies and fragments of antibodies (e.g. Fab, F(ab)$_2$, Fd and antibody fragments which include a CDR3 region which binds selectively to the osteoclast transporter proteins of the invention). Preferred isolated binding polypeptides are those that bind an extracellular portion of the osteoclast transporter proteins of the invention.

The invention in another aspect involves a method for decreasing osteoclast activity in a subject. An agent that selectively binds to an isolated nucleic acid molecule as described above or an expression product thereof is administered to a subject in need of such treatment, in an amount effective to decrease osteoclast activity in the subject. In one embodiment, the agent selectively binds to an extracellular domain of the expression product. Preferred agents are modified antisense nucleic acids and polypeptides.

The invention also contemplates gene therapy for osteopetrosis, wherein defective stem cells of a donor are genetically engineered to include an isolated nucleic acid expressing a functional osteoclast transporter protein. The cells then are returned to the donor.

In the same manner as described above kidney cell tubule activity may be modulated using the methods and products of the invention.

DETAILED DESCRIPTION OF THE INVENTION

Figure 1:
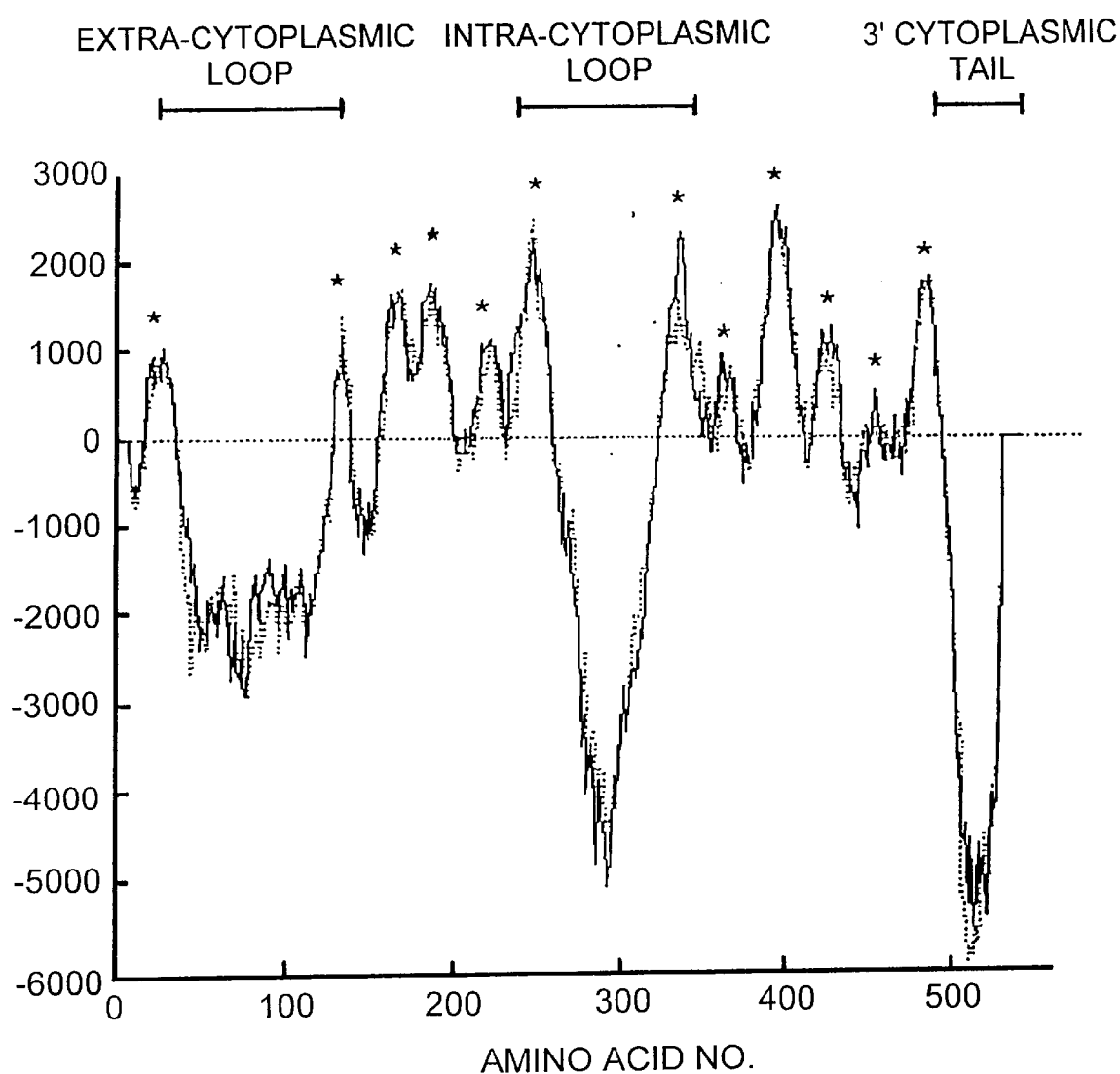
FIG. 1 is a graph depicting hydrophobicity vs. amino acid for the mouse osteoclast transporter protein.

The present invention in one aspect involves the cloning of a gene encoding an osteoclast transporter protein. The sequence of the gene (from mouse) is presented as SEQ.ID.NO. 1, and the predicted amino acid sequence of this gene's protein product is presented as SEQ.ID.NO. 2. The mRNA transcript is about 2.0 kb in length. It was obtained from mouse kidney tubule cells. A partial clone of the apparent human homolog was identified in Genbank, accession no. H20345, and is presented as SEQ.ID.NO. 3. The partial clone is available from American Type Culture Collection Depository, Rockville, Md. The predicted (partial) amino acid sequence of human protein product is presented as SEQ.ID.NO. 4, edited to remove frame shifts.

The mouse gene maps to the proximal portion of chromosome 19, in a region to which the osteosclerosis (oc) mutation has been assigned previously. The phenotype of oc/oc mutant mice includes osteopetrosis, and the osteoclasts of these mutant mice, although present, appear to be nonfunctional. The osteoclast transporter protein of the present invention is not expressed in oc/oc mutant mice, although Southern analysis indicates that the transporter locus is unrearranged and intact in these mutant mice. The osteoclast transporter protein of the present invention, however, is expressed in normal osteoclasts, and it is believed that hereditary osteopetrosis results from mutations to this gene, which impair osteoclast function.

The gene is not expressed in any other normal tissue tested, except in kidney tubule cells where its function is believed to be redundant. In particular, Northern analysis demonstrated that the gene is not expressed in normal skeletal muscle, pancreas, lung, heart, brain, stomach, spleen, salivary gland, thymus, liver, large intestine or small intestine tissue.

Searches of Genbank for similar related proteins shows that this protein shares some very limited, localized homology and sequence motifs to known proteins with transport functions. The protein of the invention, however, does have a length and tertiary structures similar to known transporters.

Specifically, it appears to be a member of a large family of genes with transport functions called the "major facilitator superfamily" by Marger and Saier, which include a number of unisym- and antiporters specific for sugars, organic acids and drugs. The common structural motif of this family are 12 transmembrane alpha helices, and often includes a central cytoplasmic loop between the 6th and 7th membrane-spanning domains. The hydrophobicity plot for the protein of the present invention is shown in FIG. 1. Each asterisk indicates a potential membrane spanning hydrophobic domain. There appears to be an extracellular loop between the first and second hydrophobic domains, an intra-cytoplasmic loop between the hydrophobic domains 6 and 7, and a 3' intra-cytoplasmic tail. The 5' end also appears to be internal within the cytoplasm.

The transporter also contains amino-acid motifs found in this class of molecules, including a sequence, D-R-F-G-R-K (SEQ ID NO:5), similar to a D-R/K-X-R-R/K sequence (SEQ ID NO:6) after the 2nd membrane domain, and a P-E-S/T sequence found after the 12th transmembrane domain. For genes with known function, the transporter is most closely related to the polyspecific rat cation transporter Oct1 (30% amino acid identity and 50% similarity), which has been shown to transport a variety of organic cationic drugs (Grundemann et al., Nature, Vol. 372, December 1994.)

The invention thus involves osteoclast transport proteins, genes encoding those proteins, functional modifications and variants of the foregoing, useful fragments of the foregoing, as well as therapeutics and diagnostics relating thereto.

Homologs and alleles of the osteoclast transporter genes of the invention can be identified by conventional techniques. Thus, an aspect of the invention is those nucleic acid sequences which code for osteoclast transporter proteins and which hybridize to a nucleic acid molecule consisting of SEQ.ID.NO. 1 or SEQ.ID.NO. 3, under stringent conditions. The term "stringent conditions" as used herein refers to parameters with which the art is familiar. More specifically, stringent conditions, as used herein, refers to hybridization at 65° C. in hybridization buffer (3.5×SSC, 0.02% FICOLL, 0.02% polyvinyl pyrolidone, 0.02% Bovine Serum Albumin, 2.5 mM $NaH_2PO_4$(pH7), 0.5% SDS, 2 mM EDTA). SSC is 0.15M sodium chloride/0.15M sodium citrate, ph7; SDS is sodium dodecyl sulphate; and EDTA is ethylenediaminetetracetic acid. After hybridization, the membrane upon which the DNA is transferred is washed at 2×SSC at room temperature and then at 0.1×SSC/0.1×SDS at 65° C.

There are other conditions, reagents, and so forth which can used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of osteoclast transporter proteins of the invention. The skilled artisan also is familiar with the methodology for screening cells and libraries for expression of such molecules which then are routinely isolated, followed by isolation of the pertinent nucleic acid molecule and sequencing.

In general homologs and alleles typically will share at least 40% nucleotide identity and/or at least 50% amino acid identity to SEQ.ID.NOS. 1 or 3 and 2 or 4, respectively, in some instances will share at least 50% nucleotide identity and/or at least 65% amino acid identity and in still other instances will share at least 60% nucleotide identity and/or at least 75% amino acid identity. Watson-Crick complements of the forgoing nucleic acids also are embraced by the invention.

In screening for osteoclast transporter protein family members, a Southern blot may be performed using the foregoing conditions, together with a radioactive probe.

After washing the membrane to which the DNA is finally transferred, the membrane can be placed against x-ray film to detect the radioactive signal.

A cDNA fragment carrying a sequence which appears to correspond to the 3' end of the human transporter has been identified (Seq.ID No. 3). Given that expression of this gene is abundant in murine kidney, it is likely that the human full-length clone corresponding to this sequence can be isolated from a human kidney cDNA library, using standard colony hybridization techniques.

The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue. Similarly, nucleotide sequence triplets which encode other amino acid residues include, but are not limited to,: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides isolated unique fragments of SEQ.ID.NO. 1, SEQ.ID.NO. 3, or compliments of SEQ.ID.NO. 1 or SEQ.ID.NO. 3. A unique fragment is one that is a 'signature' for the larger nucleic acid. It, for example, is long enough to assure that its precise sequence is not found in molecules outside of the osteoclast transporter protein family as defined by claim 1. Unique fragments can be used as probes in Southern blot assays to identify family members or can be used in amplification assays such as those employing PCR. As known to those skilled in the art, large probes such as 200 BP or more are preferred for certain uses such as Southern blots, while smaller fragments will be preferred for uses such as PCR. Unique fragments also can be used to produce fusion proteins for generating antibodies or for generating immunoassay components. Likewise, unique fragments can be employed to produce fragments of the osteoclast transporter protein such as only the extracellular portion, useful, for example, in immunoassays or as a competitive inhibitor of the substrate of the osteoclast transporter protein in therapeutic applications. Unique fragments further can be used as antisense molecules to inhibit the expression of the osteoclast transporter proteins of the invention, particularly for therapeutic purposes as described in greater detail below.

As will be recognized by those skilled in the art, the size of the unique fragment will depend upon its conservancy in the genetic code. Thus, some regions of SEQ.ID.NO. 1 and SEQ.ID.NO. 3, and their complements, will require longer segments to be unique while others will require only short segments, typically between 12 and 32 BP (e.g. 12, 13, 14, 15, 16, 17, 18, 19, 20, 21, 22, 23, 24, 25, 26, 27, 28, 29, 30, 31 and 32 bases long). Virtually any segment of SEQ.ID.NO. 1 or SEQ.ID.NO. 3, or their complements, that is 18 or more nucleotides in length will be unique. Those skilled in the art are well versed in methods for selecting such sequences, typically on the basis of the ability of the unique fragment to selectively distinguish the sequence of interest from non-family members. A comparison of the sequence of the fragment to those on known data bases typically is all that is necessary, although in vitro confirmatory hybridization and sequencing analysis may be performed.

As mentioned above, the invention embraces antisense oligonucleotides that selectively bind to a nucleic acid molecule encoding an osteoclast transporter protein, to decrease osteoclast activity. This is desirable in virtually any medical condition wherein a reduction in osteoclast activity is desirable, including when a reduction in bone loss or an increase in bone mass is desired. By decreasing the osteoclast activity in a subject, bone remodeling thus can be favorably affected. Antisense molecules, in this manner, can be used to slow down or arrest the loss in bone mass occurring with certain forms of osteoporosis and may even result in an increase in bone mass in circumstances where an increase in bone mass is desirable.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. Based upon SEQ ID NO. 1 and SEQ ID NO. 3, or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 10 and, more preferably, at least 15 consecutive bases which are complementary to the target. Most preferably, the antisense oligonucleotides comprise a complementary sequence of 20–30 bases. Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions or telomerase sites may be targeted. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., *Cell Mol. Neurobiol.* 14(5):439–457 (1994)) and at which proteins are not expected to bind. Finally, although, SEQ ID NO. 1 discloses a cDNA sequence, one of ordinary skill in the art may easily derive the genomic DNA corresponding to the cDNA of SEQ ID NO. 1. Thus, the present invention also provides for antisense oligonucleotides which are complementary to the genomic DNA corresponding to SEQ ID NO. 1. The full length cDNA corresponding to SEQ.ID.NO. 3 and corresponding genomic sequences, as well as antisense thereto, also are enabled by the present invention. Similarly, antisense to allelic or homologous cDNAs and genomic DNAs are enabled without undue experimentation.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, and carboxymethyl esters.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. The present invention, thus, contemplates pharmaceutical preparations containing modified antisense molecules that are complementary to and hybridizable with, under physiological conditions, nucleic acids encoding osteoclast transporter proteins, together with pharmaceutically acceptable carriers.

Antisense oligonucleotides may be administered as part of a pharmaceutical composition. Such a pharmaceutical composition may include the antisense oligonucleotides in combination with any standard physiologically and/or pharmaceutically acceptable carriers which are known in the art. The compositions should be sterile and contain a therapeutically effective amount of the antisense oligonucleotides in a unit of weight or volume suitable for administration to a patient. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

The invention also involves expression vectors coding for osteoclast transporter proteins and fragments and variants thereof and host cells containing those expression vectors. Virtually any cells, prokaryotic or eukaryotic, which can be transformed with heterologous DNA or RNA and which can be grown or maintained in culture, may be used in the practice of the invention. Examples include bacterial cells such as E.coli and mammalian cells such as mouse, hamster, pig, goat, primate, etc. They may be of a wide variety of tissue types, including mast cells, fibroblasts, oocytes and lymphocytes, and they may be primary cells or cell lines. Specific examples include CHO cells and COS cells. Cell-free transcription systems also may be used in lieu of cells. In gene therapy applications, human hematopoietic cells that are precursors of osteoclasts are contemplated.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g. β-galactosidase or alkaline phosphatase), and genes which visibly affect the phenotype of transformed or transfected cells, hots, colonies or plaques. Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribing and 5' non-translating sequences involved with the initiation of transcription and translation respectively, such as a TATA box, capping sequence, CAAT sequence, and the like. Especially, such 5' non-transcribing regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences, 5' or 3'. The choice and design of an appropriate vector is within the ability and discretion of one of ordinary skill in the art.

Expression vectors containing all the necessary elements for expression are commercially available and known to those skilled in the art. See Sanbrook et al., *Molecular Cloning: A Laboratory Manual*, Second Edition, Cold Spring Harbor Laboratory Press, 1989. Cells are genetically engineered by the introduction into the cells of heterologous DNA (RNA) encoding the osteoclast transporter protein or fragment or variant thereof. That heterologous DNA (RNA) is placed under operable control of transcriptional elements to permit the expression of the heterologous DNA in the host cell. In still another aspect of the invention, a defective osteoclast or precursor thereof is treated with DNA in a manner to promote via homologous recombination intracellularly the correction of a defective osteoclast transporter gene.

Preferred systems for mRNA expression in mammalian cells are those such as pRc/CMV (available from Invitrogen, San Diego, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen), which contains an Epstein Barr virus (EBV) origin of replication, facilitating the maintenance of plasmid as a multicopy extrachromosomal element.

mRNA expression and transporter function can be tested using these vectors in a wide variety of mammalian cell lines. Preferred systems include cells derived from kidney tubules, including MDCK and IMCD-3 cells (both available from ATCC).

A variety of systems for expression of proteins in bacterial, yeast, mammalian, or insect cells have been described and are commercially available. Preferred systems include the Glutathione-S-transferase (GST) Gene Fusion system available from Pharmacia Biotech, Piscataway, N.J. In this system a plasmid is constructed containing the protein sequence of interest (in this case, the transporter including the first extracellular domain) inserted in frame downstream of the 25 kDa GST domain from *S. japonicum*. Expression of the fusion protein can be induced in transfected bacterial cells and the fusion protein purified by affinity chromatography using Glutathione Sepharose 4B. Cleavage of the desired peptide from the GST sequences is achieved using a site specific protease whose recognition sequence is located immediately upstream from the cloning site. An alternative system which is desirable since it maintains eucaryotic-specific functions such as glycosylation is recombination into baculovirus. Standard protocols exist (c.f. O'Reilly et al., Baculovirus Expression Vectors: A : Laboratory Manual, IRL/Oxford University Press, 1992) and vectors, cells, and reagents are commercially available.

The invention also involves polypeptides which bind to osteoclast transporter proteins and in certain embodiments preferably to the extracellular domain of the proteins. Such binding partners can be used in screening assays to detect the presence or absence of the osteoclast transporter protein and in purification protocols to isolate osteoclast transporter proteins. Such binding partners also can be used to inhibit the native activity of the osteoclast transporter protein by binding to the extracellular domain of such proteins. Likewise, such binding partners can be used to selectively target drugs, toxins or other molecules to osteoclasts. In this manner, osteoclast activity may be selectively increased by drugs that would enhance osteoclast activity or selectively impaired by drugs that would inhibit osteoclast activity (e.g. toxins, antisense, etc.). In this manner, bone remodeling may be desirably affected.

The invention, therefore, involves antibodies or fragments of antibodies having the ability to selectively bind to osteoclast transporter proteins, and preferably to the extracellular domain thereof. Antibodies include polyclonal and monoclonal antibodies, prepared according to conventional methodology.

Significantly, as is well-known in the art, only a small portion of an antibody molecule, the paratope, is involved in the binding of the antibody to its epitope (see, in general, Clark, W. R. (1986) *The Experimental Foundations of Modem Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an $F(ab')_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for $F(ab')_2$, Fab, Fv and Fd fragments; chimeric antibodies in which the Fc and/or FR and/or CDR1 and/or CDR2 and/or light chain CDR3 regions have been replaced by homologous human or non-human sequences; chimeric $F(ab')_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies. Thus, the invention involves polypeptides of numerous size and type that bind specifically to osteoclast transporter proteins. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent a completely degenerate or biased array. One then can select phage-bearing inserts which bind to the osteoclast transporter protein. This process can be repeated through several cycles of reselection of phage that bind to the osteoclast transporter protein. Repeated rounds lead to enrichment of phage bearing particular sequences. DNA sequence analysis can be conducted to identify the sequences of the expressed polypeptides. The minimal linear portion of the sequence that binds to the osteoclast transporter protein can be determined. One can repeat the procedure using a biased library containing inserts containing part or all of the minimal linear portion plus one or more additional degenerate residues upstream or downstream thereof. Thus, the osteoclast transporter molecule of the invention, an extracellular domain thereof, or the like, can be used to screen peptide libraries, including phage display libraries, to identify and select peptide binding partners of the extracellular portion of the osteoclast transporter protein of the invention. Such molecules can be used, as described, for screening assays, for diagnostic assays, for purification protocols, for interfering directly with the functioning of osteoclasts by binding to the osteoclast transporter protein or for targeting drugs, toxins and/or labeling agents (e.g. radioisotopes, fluorescent molecules, etc.) to osteoclasts and/or osteoclast transporter proteins. Drug molecules that would affect osteoclast activity and toxin molecules that would disable or destroy osteoclast cells are known to those skilled in the art and are commercially available. For example, the immunotoxin art provides examples of toxins which are effective when delivered to a cell by an antibody or fragment thereof. Examples of toxins include ribosome-damaging toxins derived from plants or bacterial such as ricin, abrin, saporin, Pseudomonas endotoxin, diphtheria toxin, A chain toxins, blocked ricin, etc.

Osteoclast activity can be assayed both in vitro and in vivo. Heterogeneous culture systems in which bone marrow derived cells are co-cultured with osteoblast cells in the presence of 1,25-dihydroxyvitamin D3 will generate mature osteoclasts, whose activity can be quantitated by measuring their ability to form resorption pits on dentine slices (Takahashi et al., Endocrinology, Vol. 122, No. 4, 1988). In mammals, decreased osteoclast function results in the clinical condition of osteopetrosis. In rodents, this can be readily scored by virtue of the fact that, in this case, incisors fair to erupt after birth. Thus, rodent neonates can be treated with compositions of the invention and the effect on osteoclast activity can be determined by scoring incisor eruption. The degree of osteopetrosis can be more accurately quantitated by morphometrical analysis of the bone marrow space (Boyce et al., J. Clin. Invest., Vol. 90, 1992).

When used therapeutically, the compounds of the invention are administered in therapeutically effective amounts. In general, a therapeutically effective amount means that amount necessary to delay the onset of, inhibit the progression of, or halt altogether the particular condition being treated. Therapeutically effective amounts specifically will be those which desirably influence osteoclast activity. When it is desired to decrease osteoclast activity, then any inhibition of osteoclast activity is regarded as a therapeutically effective amount. When it is desired to increase osteoclast activity, then any enhancement of osteoclast activity is regarded as a therapeutically effective amount. Generally, a therapeutically effective amount will vary with the subject's age, condition, and sex, as well as the nature and extent of the disease in the subject, all of which can be determined by one of ordinary skill in the art. The dosage may be adjusted by the individual physician or veterinarian, particularly in the event of any complication. A therapeutically effective amount typically varies from 0.01 mg/kg to about 1000 mg/kg, preferably from about 0.1 mg/kg to about 200 mg/kg and most preferably from about 0.2 mg//kg to about 20 mg/kg, in one or more dose administrations daily, for one or more days.

The therapeutics of the invention can be administered by any conventional route, including injection or by gradual infusion over time. The administration may, for example, be oral, intravenous, intraperitoneal, intramuscular, intracavity, subcutaneous, or transdermal. When antibodies are used therapeutically, a preferred route of administration is by pulmonary aerosol. Techniques for preparing aerosol delivery systems containing antibodies are well known to those of skill in the art. Generally, such systems should utilize components which will not significantly impair the biological properties of the antibodies, such as the paratope binding capacity (see, for example, Sciarra and Cutie, "Aerosols," in *Remington's Pharmaceutical Sciences*; 18th edition, 1990, pp 1694–1712; incorporated by reference). Those of skill in the art can readily determine the various parameters and conditions for producing antibody aerosols without resort to undue experimentation. When using antisense preparations of the invention, slow intravenous administration is preferred.

Preparations for parenteral administration include sterile aqueous or non-aqueous solutions. suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The invention also contemplates gene therapy. The procedure for performing ex vivo gene therapy is outlined in U.S. Pat. No. 5,399,346 and in exhibits submitted in the file history of that patent, all of which are publicly available documents. In general, it involves introduction in vitro of a functional copy of a gene into a cell(s) of a subject which contains a defective copy of the gene, and returning the genetically engineered cell(s) to the subject. The functional copy of the gene is under operable control of regulatory elements which permit expression of the gene in the genetically engineered cell(s). Numerous transfection and transduction techniques as well as appropriate expression vectors are well known to those of ordinary skill in the art, some of which are described in PCT application WO95/00654. In vivo gene therapy using vectors such as adenovirus also is contemplated according to the invention.

Thus, defective osteoclasts or precursors thereof are provided with a non-defective nucleic acid encoding an osteoclast transporter protein. In particular, such gene therapy is appropriate for hereditary forms of osteopetrosis involving defective osteoclast transporter protein genes. For example, primary human blood cells which are precursors of osteoclasts can be obtained from the bone marrow of a subject who is a candidate for such gene therapy. Candidates can be identified by screening for abnormal osteoclast function that results from a defective osteoclast transporter protein. Then, such cells can be genetically engineered ex vivo with DNA (RNA) encoding a normal osteoclast transporter protein. The genetically engineered cells then are returned to the patient.

That the transporter can be used to correct the defect in the clinical conditions of osteopetrosis in which it has been inactivated is demonstrated using a mouse model system. The osteosclerosis (oc) mutant mouse fails to express the transporter and has osteopetrosis. The transporter is introduced into a vector such as pXT1 (Strategene, La Jolla, Calif.) that, when transfected into an appropriate packaging cell line, will generate a higher titer of replication-defective retrovitral particles carrying the transporter under the regulatory control of a thymidine kinase promoter. Hematopoietic progenitor cells from oc mutant mice are prepared and, using well-documented techniques of infection and selection, stem cells carrying this vector are selected after coculture with the retrovirus. Re-population of lethally irradiated oc mutant mice with this transfected population is accomplished using documented protocols of hematopoietic transplantation, and the degree of amelioration of the osteopetrosis phenotype then is determined by radiography and morphometrical analysis.

While the invention has been described with respect to certain embodiments, it should be appreciated that many modifications and changes may be made by those of ordinary skill in the art without departing from the spirit of the invention. It is intended that such modification, changes and equivalents fall within the scope of the following claims.

We claim:

1. An isolated nucleic acid molecule selected from the group consisting of
   (a) nucleic acid molecules which hybridize under stringent conditions to a molecule consisting of the nucleotide sequence of SEQ.ID.NO. 1 and which code for an osteoclast transporter molecule,
   (b) nucleic acid molecules that differ from the nucleic acid molecules of (a) in codon sequence due to the degeneracy of the genetic code, and
   (c) complements of (a) and (b).

2. An expression vector which comprises the isolated nucleic acid molecule of claim 1 operably linked to a promoter.

3. A host cell transformed or transfected in vitro with an expression vector comprising the isolated nucleic acid molecule of claim 1, operably linked to a promoter.

4. The isolated nucleic acid molecule of claim 1, wherein the isolated nucleic acid molecule comprises SEQ.ID.NO. 3.

5. An expression vector which comprises the isolated nucleic acid molecule of claim 4 operably linked to a promoter.

6. A host cell transformed or transfected in vitro with an expression vector comprising the isolated nucleic acid molecule of claim 4, operably linked to a promoter.

7. The isolated nucleic acid molecule of claim 1, wherein the isolated nucleic acid molecule comprises SEQ.ID.NO. 1.

8. An expression vector which comprises the isolated nucleic acid molecule of claim 1 operably linked to a promoter.

9. A host cell transformed or transfected in vitro with an expression vector comprising the isolated nucleic acid molecule of claim 7, operably linked to a promoter.

10. An isolated nucleic acid molecule selected from the group consisting of (a) a unique fragment of SEQ.ID.NO. 1 between 20 and 1974 nucleotides in length, (b) a unique fragment of SEQ.ID.NO. 3 between 20 and 360 nucleotides in length, (c) complements of "(a)" and (d) complements of "(b)", wherein the unique fragment encodes a fragment of an osteoclast transporter protein.

11. The isolated nucleic acid molecule of claim 10 wherein the isolated nucleic acid molecule is selected from the group consisting of at least 22 contiguous nucleotides of (a) SEQ.ID.NO. 1, (b) SEQ.ID.NO. 3, (c) complements of "(a)", and (d) complements of "(b)".

12. The isolated nucleic acid molecule of claim 10, wherein the isolated nucleic acid molecule is selected from the group consisting of between 20 and 32 contiguous nucleotides of (a) SEQ.ID.NO. 1, (b) SEQ.ID.NO. 3, (c) complements of "(a)", and (d) complements of "(b)".

* * * * *